United States Patent [19]

Moore

[11] Patent Number: Plant 5,680

[45] Date of Patent: Mar. 4, 1986

[54] GRAPEVINE—MARS CULTIVAR

[75] Inventor: James N. Moore, Fayetteville, Ark.

[73] Assignee: University of Arkansas Agricultural Experiment Station, Fayetteville, Ark.

[21] Appl. No.: 628,142

[22] Filed: Jul. 5, 1984

[51] Int. Cl.[4] ..... A01H 5/00
[52] U.S. Cl. ..... Plt./47
[58] Field of Search ..... Plt./47

*Primary Examiner*—James R. Feyrer

[57] ABSTRACT

Description and specifications of a new and distinct grapevine variety which originated from seed produced by a hand-pollinated cross of Island Belle (non-patented) and Arkansas Selection 1339 (non-patented) is provided. This new grapevine variety can be distinguished by its early ripening fruit, its attractive blue fruit color, and by its outstanding resistance to foliar and fruit diseases.

2 Drawing Figures

SUMMARY OF THE INVENTION

The new and distinct variety of grapevine originated from a hand pollinated cross of Island Belle (non-patented) × Arkansas selection 1339 (non-patented), made in 1972 at the Arkansas Agricultural Experiment Station experimental vineyard at Clarksville, Ark. The seeds resulting from this controlled hybridization were germinated in a greenhouse during the winter of 1972–1973. Resulting seedlings were planted in the spring of 1973 in a field on the Arkansas Agricultural Experiment Station at Clarksville, Ark. The seedlings fruited in the summer of 1975 and one, designated Ark. 1508, was selected for its outstanding resistance to diseases, and its good fruit quality and seedless fruit.

During 1976, the original plant selection was propagated asexually by rooting hardwood cuttings and a test planting of four vines was established. Subsequently larger test plantings have been established with asexually multiplied vines at four additional locations in Arkansas and on state agricultural experiment stations in Texas, New York, Missouri, North Carolina, Minnesota, Indiana, Florida and South Dakota.

The new variety has been asexually propagated annually since 1976 by the rooting of both hardwood and softwood cuttings and by grafting onto rootstocks. It roots readily from both hardwood and softwood cuttings and no graft incompatibility has been observed. During all types of asexual multiplication, the vegetative and fruit characteristics of the original plant have been maintained.

Test plantings over a wide geographic area have shown this new variety to be widely adapted to differing soil and climatic conditions. It has shown above average winter hardiness for a seedless grape. The canes mature their wood early and enter winter in a well-hardened condition.

Vines of the new variety are vigorous and typically characteristic of *Vitis labrusca*. It has produced well as own-rooted plants in all locations tested except on the calcareous soils of southwest Texas, where it must be grafted onto a rootstock. Vines are precocious in bearing, and good production is obtained during the early years after planting. Due to their precocity, young vines may overproduce and require cluster thinning.

A distinctive feature of the new variety is its resistance to common fungus diseases of grapevines. Under minimum chemical disease control, the vines and fruit have demonstrated outstanding resistance to black rot (*Guignardia bidwellii* (Ell.) V. & R.), anthracnose (*Elsinoe ampelina* (d. By.) Sher), powdery mildew (*Uncinula necator* Burr.) and downy mildew (*Plasmopora viticola* Berl. & Tomi.). The fruit has shown no inclination to split following rains.

The new variety ripens its fruit early, about 3 days before the Fredonia cultivar. The average ripening date is July 22 in central Arkansas. The fruit quality is maintained well on the vine after maturity. Berries adhere well to the fruit pedicels and do not shatter from the clusters.

The fruit is an attractive blue color at maturity. The fruit shape is round. Fruit skins are medium thick and do not adhere to the flesh. The fruit is of the stenospermocarpic type of seedlessness and contains very small vestigial seed traces that are not noticeable when eaten. The berries are large in size (ca. 3.5 g) for a seedless grape. The flavor is strong and typically labrusca in character, resembling somewhat that of the variety Campbell's Early. Soluble solids content of the fruit is only medium (ca. 16%) but acid content is low and the fruit tastes sweet.

Fruit clusters, borne usually two per shoot, are medium in size (ca. 220 g), well-filled, and compact. Fruit cluster peduncles are short and the clusters form close to the supporting shoots.

The new variety has been named the MARS cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the pomological characteristics of the subject grapevine. Color terminology is in accordance with that of The Royal Horticultural Society Colour Chart published in 1966 by The Royal Horticultural Society of London, England.

Where dimensions, sizes, colors and other characteristics are given, it is to be understood that such characteristics are approximations of averages set forth as accurately as practicable.

The description reported herein are from specimens grown at Clarksville, Ark.

Vine:

*Size.*—Medium.

*Growth.*—Medium vigor, cessation in early fall.

*Productivity.*—Medium-high (15-18 MT/ha on mature vines). Young vines precocious.

*Cold hardiness.*—Above average for seedless grapes. Equal to Concord variety.

*Canes.*—Medium diameter, long, not upright in growth habit. Diameter of mature cane: base 9.5 mm, midpoint 6.9 mm, terminal 2.4 mm. Internode length: base 2.6 cm, midpoint 8.8 cm, terminal 4.5 cm. Color of mature cane: base brown (200C), midpoint brown (200C), terminal brown (200C). Color of growing shoot in spring: base yellow green (146C), terminal yellow green (144A).

*Disease resistance.*—Outstanding resistance to fungus diseases black rot, downy mildew, powdery mildew, and anthracnose.

Foliage:

*Leaves.*—Color — Older leaves near base of shoot are yellow green (146A) on upper surface and yellow green (148C) on lower surface. Sub-terminal fully expanded leaves are yellow green (146C) on upper surface and yellow green (145C) on lower surface. Petioles are yellow green (145C) on both mature and young leaves. Sinus of mature leaf at base of cane is 4.5 cm deep and 4.8 cm wide at widest point.

Flowers:

*Date of first bloom.*—May 13.

*Date of last bloom.*—May 23.

*Blossom color.*—Yellow green (144C).

*Shape of cluster.*—Short conic, slight taper, rarely with shoulder.

*Size of cluster.*—Length: 11-16 cm, ave. 13 cm. Width: 9-14 cm, ave. 11 cm. Weight: 223 g.

Character: compact, well-filled. Number of berries: 64.

*Reproductive organs.*—Stamens — Medium and erect. Pistils — Medium long. Pollen — Normal. Type of seedlessness — Stenospermocarpy.

Fruit:

*Maturity.*—Early, 3 days before Fredonia. Average ripe date July 22.

*Size of berry.*—Medium-large, ave. 3.5 g, larger than Suffolk Red and Canadice, uniform in size.

*Shape.*—Spherical, uniform shape.

*Color.*—Blue at maturity (Blue Group 103A).

*Skin.*—Medium thick, non-adhering to flesh.

*Character of seeds.*—Stenospermocarpic seedless, very small vestigial seeds present but not lignified and unnoticeable when eaten.

*Flesh.*—Melting texture.

*Flavor.*—Typically labrusca, strong, similar to Campbell's Early variety.

*Soluble solids.*—16%.

*Total acids.*—0.83%.

*Eating quality.*—Good.

*Storage quality.*—Undetermined.

*Berries per cluster.*—64.

*Clusters per vine.*—62.

*Clusters per shoot.*—Usually 2.

*Uses.*—Fresh table grape and raisins. Especially suitable for home gardens because of high disease resistance.

The variety: The most distinctive features of the variety are its high resistance to fungus diseases, its cold hardiness, and its good fruit quality and size.

I claim:

1. A new and distinct variety of grapevine, substantially as illustrated and described, characterized by its early ripening, large seedless fruit, and outstanding resistance to common grape fungus pathogens.

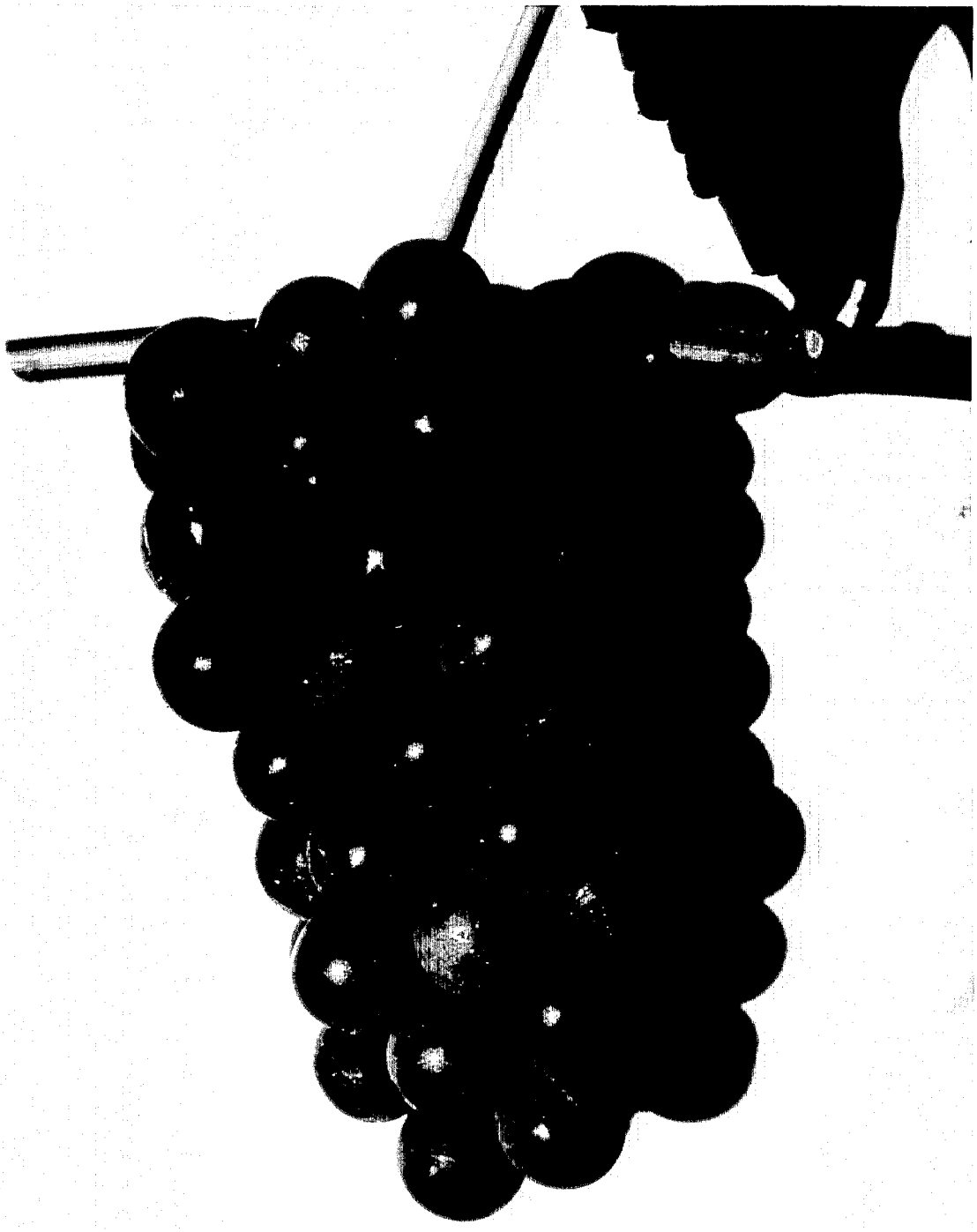

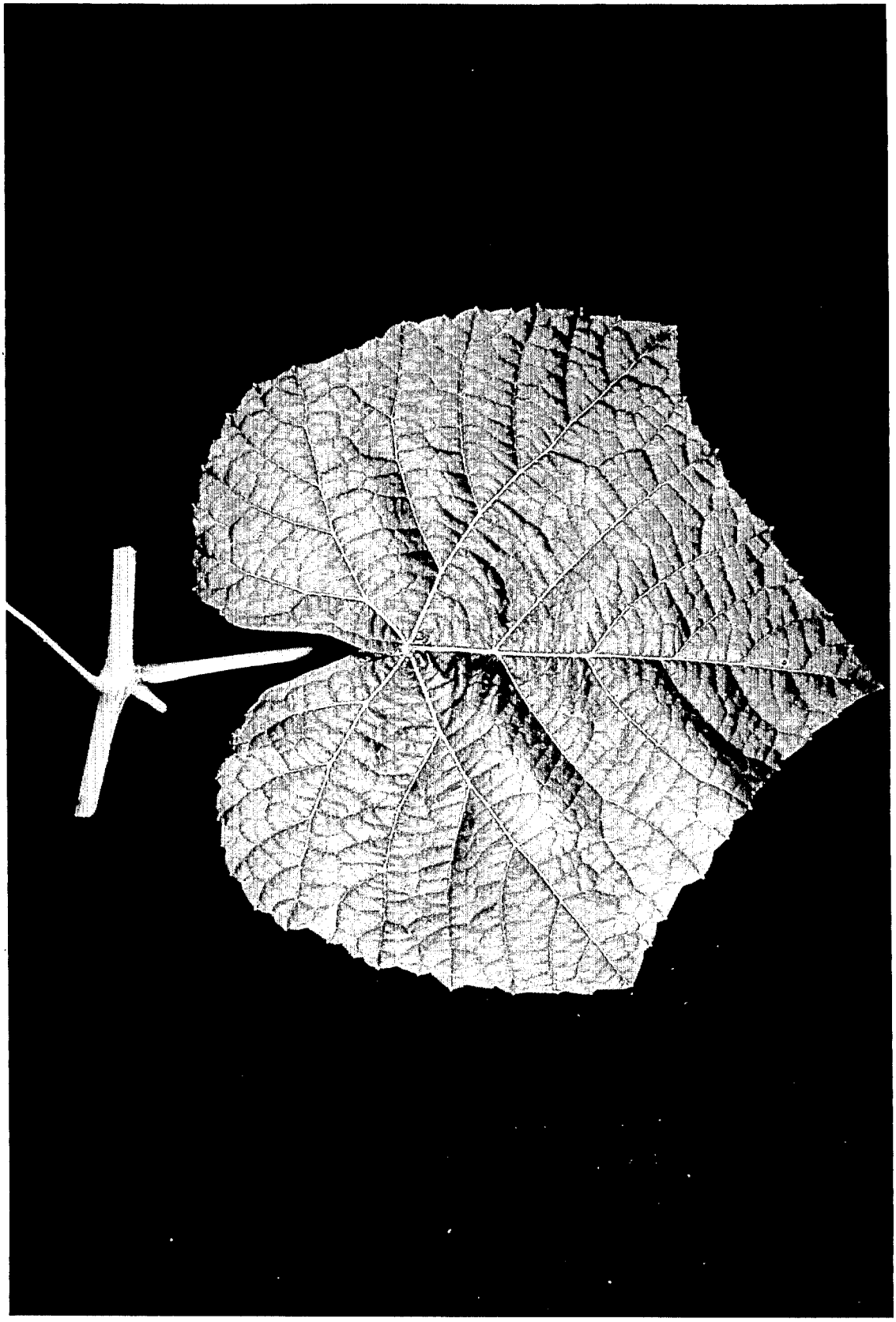

* * * * *